United States Patent [19]

Hammer et al.

[11] Patent Number: 5,536,877
[45] Date of Patent: Jul. 16, 1996

[54] PREPARATION OF ARYLBENZYLAMINES

[75] Inventors: Karl-Heinz Hammer, Rödersheim-Gronau; Gerd Husslein, Bad Dürkheim, both of Germany

[73] Assignee: BASF Aktiengesellschaft, Ludwigshafen, Germany

[21] Appl. No.: 409,090

[22] Filed: Mar. 23, 1995

[30] Foreign Application Priority Data

Mar. 25, 1994 [DE] Germany .......................... 44 10 360.3

[51] Int. Cl.$^6$ ................................................ C07C 209/08
[52] U.S. Cl. ........................... 564/386; 564/220; 564/391
[58] Field of Search ..................................... 564/386, 220, 564/391

[56] References Cited

U.S. PATENT DOCUMENTS

| | | | |
|---|---|---|---|
| 1,854,553 | 4/1932 | Livingston | 564/386 |
| 4,067,903 | 1/1978 | Hoch et al. | 564/402 |
| 4,564,706 | 1/1986 | Ecsery et al. | 564/386 X |
| 5,210,305 | 5/1993 | Desmurs, et al. | 564/404 |

FOREIGN PATENT DOCUMENTS

| | | |
|---|---|---|
| 0353131A1 | 1/1990 | European Pat. Off. . |
| 2606363 | 9/1977 | Germany . |
| 57214 | 6/1969 | Poland . |

OTHER PUBLICATIONS

Synthesis, vol. 12, Dec. 1983, pp. 1013–1014, Giuseppe TRAPANI, et al., "Trimethylamine–Borane as Useful Reagent in the N–Acylation or N–Alklation of Amines by Carboxylic Acids".

J. Chem. Tech. Biotechnol., vol. 51, 1990, pp. 293–300, N. R. Ayyangar, et al., "N–Benzyl–N–Ethylaniline; An Alternative Synthetic Approach".

Journal of Organic Chemistry vol. 44, No. 7, 30. Mar. 1979, pp. 1143–1146, E. MacCarone et al., *Steric Hindrance in the Benzlation of Anilines.*

*Primary Examiner*—Richard L. Raymond
*Attorney, Agent, or Firm*—Oblon, Spivak, McClelland, Maier, & Neustadt

[57] ABSTRACT

A process for the preparation of arylbenzylamines by the reaction of arylamines with a benzyl chloride, wherein the reaction is carried out in the presence of both a phase-transfer catalyst and a base selected from the group consisting of the inorganic bases and salts of weak organic acids.

5 Claims, No Drawings

PREPARATION OF ARYLBENZYLAMINES

The invention relates to an improved process for the preparation of arylbenzylamines by the reaction of arylamines with benzyl chloride in the presence of both a base and a phase-transfer catalyst.

Several processes are known for the preparation of arylbenzylamines. Arylbenzylamines can be obtained, for example, by condensing arylamines with benzyl chloride in the presence of a base such as magnesium oxide (cf PL 57,214).

Furthermore, arylbenzylamines can be prepared by the reaction of arylamines with benzyl alcohols in the presence of triphenyl phosphite (cf DE-A 2,606,363).

A further possibility for the preparation of arylbenzylamines consists in the reductive alkylation of benzylamines or benzyl Schiff bases (cf Trapani et al, *Synthesis*, Vol. 12 (1983), pp. 1013 et seq: Ayyangar et al, *J. Chem. Technol. Biotechnol.* Vol. 51 (1991), No 3, pp 293et seq.).

A drawback of the known processes is that the reaction mixture present after the chemical reaction contains the desired arylbenzylamine in a purity which is in most cases inadequate for direct further use, so that further processing steps are required. Thus, for example, N-benzyl-N-ethylaniline is produced by the above process in admixture with solvents, unconverted starting materials and by-products and must be distilled prior to further use.

It was thus the object of the present invention to provide a process which produces arylbenzylamines of high purity in good space-time yields.

Accordingly, we have found a process for the preparation of an arylbenzylamine by the reaction of an arylamine with a benzyl chloride, in which the reaction is carried out in the presence of both a phase-transfer catalyst and a base selected from the group consisting of the inorganic bases and salts of weak organic acids.

According to the invention, suitable arylamines are primary or secondary arylamines, where the aryl radical(s) can be optionally substituted.

In a preferred embodiment of the process of the invention the arylamine used is an N-alkylarylamine optionally substituted in the aryl radical.

Examples of suitable N-alkylarylamines are N-ethylaniline, N-methylaniline, N-ethyl-o-toluidine, N-ethyl-4-chloroaniline, 4-methoxyaniline, and 4-acetylaminoaniline. Particularly preferred N-alkylarylamines for the process of the invention are N-methylaniline and N-ethylaniline.

The arylamines can be used individually or as a mixture. Advantageously, the arylamines are used individually in the process of the invention.

The benzyl chloride used in the process of the invention is an unsubstituted benzyl chloride or a benzyl chloride substituted in the phenyl ring. Examples of suitable substituted benzyl chlorides are o- and p- chlorobenzyl chlorides, p-nitrobenzyl chloride and o-methylbenzyl chloride. It is preferred to use unsubstituted benzyl chloride.

The starting materials used in the process of the invention, ie benzyl chloride and an arylamine, are usually employed in stoichiometric ratio or with an excess of benzyl chloride of up to 5 mol %.

According to the invention, suitable bases selected from the group consisting of the inorganic bases and the salts of weak organic acids (referred to below collectively as the bases of the invention) are, eg, hydroxides, basic oxides, hydrogen phosphates, acetates, carbonates and bicarbonates of metals. It is preferred to use inorganic bases. Preferred bases in this group are carbonates or bicarbonates of alkali metals or alkaline earth metals. Particularly preferred bases in this group are alkali metal carbonates, especially sodium carbonate.

The bases of the invention are usually used in a stoichiometric ratio or in molar excess. The base is preferably used in an amount of from 1 to 2 mol per mole of arylamine, more preferably from 1.01 to 1:1 tool per mole of arylamine. The base is generally used in the form of an aqueous solution or as solid material. Advantageously, the bases of the invention are used as aqueous solutions in order to avoid incrustations on parts of the equipment and material abrasion.

The phase-transfer catalyst used can be any of the conventionally used phase-transfer catalysts. Examples of particularly suitable phase-transfer catalysts are tetrabutylammonium chloride or bromide, dibenzyldimethylammonium chloride, benzyltrimethylammonium chloride, benzyldimethyl-$C_{12}$-$C_{14}$-alkylammonium chloride. Of these, the use of benzyldimethyl-$C_2$-$C_{14}$-alkylammonium chloride is preferred. The phase-transfer catalysts, which are usually solid in pure form, can be used as such or, preferably, in dissolved form.

In a particularly preferred embodiment of the process of the invention the reaction mixture contains at least one tertiary amine and the phase-transfer catalyst is produced in situ by the reaction of the tertiary amine with the optionally substituted benzyl chloride.

The precursor of the phase-transfer catalyst can thus be added to the reaction mixture as a tertiary amine in liquid form, which reacts with benzyl chloride to produce the active quaternary compound.

The compounds preferably used for this purpose are tertiary aliphatic amines such as triethylamine, tripropylamine, tributylamine, dimethyldodecylamine, dimethyl-$C_{12}$-$C_{14}$-alkylamine ("dimethyl palm oil amine").

The phase-transfer catalyst is generally used in an amount of from 0.5 to 5 wt %, preferably from 1 to 2 wt %, based on arylamine.

In a particularly preferred embodiment of the process of the invention N-ethylaniline is caused to react with benzyl chloride to produce ethylphenylbenzylamine, the phase-transfer catalyst precursor used being N,N-dimethyldodecylamine and the inorganic base sodium carbonate.

The process of the invention is advantageously carried out without any additional organic solvent. If desired, however, organic solvents which are inert under the reaction conditions, preferably solvents that are immiscible or hardly miscible with water such as toluene or 1,2-dichloroethane can be used.

Thus the process of the invention preferably involves the use of only the arylamine, benzyl chloride and the base of the invention, optionally present as an aqueous solution, and the phase-transfer catalyst or a tertiary amine used for its production in situ.

The process of the invention can be carried out with or without water acting as diluent.

The process of the invention can be carried out at a constant temperature or with the use of a temperature profile. In this case the reaction is usually carried out at elevated temperatures preferably ranging from 80° to 110° C. and more preferably from 90° to 100° C.

When the process of the invention is carried out at temperatures ranging from 80° to 110° C. the pale color of the resulting crude arylbenzylamine remains on storage even when no special precautionary measures are taken, such as the use of a blanket of nitrogen.

The process of the invention can be carried out with or without applied pressure.

The process of the invention can be carried out, for example, as follows:

The base of the invention, eg, an inorganic base, is dissolved in a quantity of water. The arylamine and the catalyst (preferably a tertiary amine in the form of a precursor), are then added, and the mixture is heated while the benzyl chloride is fed in at ca 80° C. at such a rate that the reaction mixture heats us, due to the slightly exothermal reaction, to from 94° to 96° C. and can be kept at this temperature. The reaction is allowed to continue at ca 95° C. until conversion is complete, more cold water is optionally added to effect dissolution of the inorganic constituents and for cooling purposes, and the organic phase containing the desired benzylamine is then separated at ca 30° C. in the usual manner.

The arylbenzylamines produced by the process of the invention are valuable starting materials for dyes and auxiliaries. Thus the crude N-benzyl-N-ethylaniline prepared as described above can, for example, be directly converted to the sulfo acid, which converts to food dyes and utility dyes (eg, triphenylmethane dyes for sanitary applications).

The process of the invention has numerous advantages. Compared with the prior processes the process of the invention yields arylbenzylamines in higher yield and purity in a simple and economical manner.

The industrial plants required for this purpose are simple and can be limited to a stirred apparatus and an exhaust air cooler, whilst the material problem occurring in the prior processes at high temperatures does not occur.

Monitoring or regulation of the pH of the reaction is not generally required. The good quality of the crude arylbenzylamines produced is achieved reliably and without increased monitoring means, since even in the case of deviation from the specified ratios of starting materials the formation of the by-products to be expected (benzyl alcohols, dibenzyl ether) is almost completely suppressed. Dosage errors occurring when feeding the base used and the arylamine and benzyl chloride or deviations from the specified process parameters can therefore be corrected at all times without reduction of quality.

EXAMPLES

Example 1

In a stirred apparatus of steel/enamel there were placed 1750 parts by weight of water. To this there were added, with stirring, 750 parts by weight of sodium carbonate. Then 1400 parts by weight of N-ethylaniline and 38 parts by weight of N,N-dimethyl-$C_{12}$–$C_{14}$-alkylamine were added and the mixture was heated to 80° C. with stirring. 1496 parts by weight of benzyl chloride were then added (feed rate: 700 parts by weight per hour). The reaction mixture heated up and was kept at a temperature of from 94° to 96° C. by cooling. On completion of the addition, stirring was continued for 12 hours at this temperature. 500 parts by weight of water were then added and the reaction mixture was cooled to 30° C. The stirrer was then stopped and the mixture was allowed to stand for 1 hour to cause phase separation. The bottom aqueous phase was passed on to a regeneration stage. The top pale yellow organic phase consisted of 96wt % of N-benzyl-N-ethylaniline, 0.5 wt % of benzyl chloride, 0.5 wt % of N-ethylaniline, 2 wt % of benzyl alcohol, and 1 wt % of dibenzyl ether. The organic phase could be reused without further purification, eg, for sulfonation to N-benzyl-N-ethylaniline sulfo acid.

Example 2

In a stirred apparatus of steel/enamel there were placed 1400 parts by weight of N-ethylaniline and 38 parts by weight of N,N-dimethyl-$C_{12}$–$_{14}$-alkylamine. 750 parts by weight of sodium carbonate were added with stirring. The mixture was then heated to 90° C. and 1496 parts by weight of benzyl chloride were added sufficiently slowly to ensure that the temperature stayed at ca 95° C. Stirring was then carried out for 10 hours at 95° C. and 14 hours at 110° C. The reaction mixture was then allowed to flow into a quantity of 2500 parts by weight of water and the phases were separated as described in Example 1. The reaction mixture consisted of more than 99 wt % of N-benzyl-N-ethylaniline.

Example 3 (for comparison)

To a quantity of 1380 parts by weight of N-methyl aniline there were introduced 1620 parts by weight of benzyl chloride and 99 parts by weight of sodium carbonate. Stirring was then continued over a period of 4 h at 105°–110° C. and the mixture was cooled to 40° C. Following the addition of 5000 parts by weight of water the phases formed were separated and the organic product phase was stirred with 130 parts by weight of activated charcoal and 2560 parts by weight of water. Following the removal, by filtration, of the solid components the mixture was topped up with water to 15000 parts by weight, stirring was continued and the lower organic phase was separated. There were obtained 2250 parts by weight of a product having the following composition: 87.1 wt % of N-methyl-N-benzylaniline, 6.2 wt % of benzyl chloride, 4.8 wt % of N-methyl aniline, and 0.3 of benzyl alcohol.

Example 4

To a quantity of 750 parts by weight of sodium carbonate in 1750 parts by weight of water there were added 1237 parts by weight of N-methyl aniline and 30 parts by weight of dimethyl-$C_{12}$–$C_4$-amine. After heating to 80° C. 1496 parts of benzyl chloride were metered in at such a rate over a period of 2 h that the temperature of the reaction mixture rose to 94°–96° C. and rose no further over the rest of the feed-in period. Stirring was continued for 12 h at 95° C. and the mixture was cooled to 50° C., there were added 500 parts by weight of water, with stirring, the mixture was cooled to 30°–35° C., and the organic phase was separated. There were obtained 2250 parts by weight of a product having the following composition: 97.5 wt % of N-methyl-N-benzylaniline, 0.6 wt % of benzyl chloride, 0.8 wt % of N-methyl aniline, and 0.3 % of benzyl alcohol.

Example 5

To a quantity of 1237 parts by weight of N-methyl aniline there were introduced at ambient temperature, with stirring, 750 parts by weight of sodium carbonate and 30 parts by weight of dimethyl-$C_{12}$–$C_{14}$-amine. After heating to 90° C. 1496 parts by weight of benzyl chloride were metered at such a rate over a period of 2 h that the temperature of the reaction mixture rose to 94°–96° C. and rose no further over the rest of the feed-in period. Stirring was then continued for 5 h at 95° C. and a further 20 h at 105°–110° C. By adding 2500 parts by weight of cold water the mixture was cooled to 50° C. with stirring and the organic phase was separated after standing for 30 min. There were obtained 2270 parts by weight of a product having the following composition: 99.1 wt % of N-methyl-N-benzylaniline, 0.2 wt % of benzyl chloride, 0.15 wt % of N-methyl aniline, and 0.3 wt % of benzyl alcohol.

We claim:

1. A process for the preparation of N-alkyl-N-benzylarylamines by the reaction of N-alkylarylamines with a benzyl chloride, wherein the reaction is carried out in the presence of both a phase-transfer catalyst and a base selected from the group consisting of the inorganic bases and salts of weak organic acids.

2. A process as defined in claim 1, wherein the inorganic base used is an alkali metal and/or alkaline earth metal carbonate or bicarbonate.

3. A process as defined in claim 2, wherein the inorganic base used is an alkali metal carbonate.

4. A process as defined in claim 1, wherein the arylamine used is an N-alkylaniline optionally substituted in the phenyl ring.

5. A process as defined in claim 1, wherein the reaction mixture contains at least one tertiary amine and the phase-transfer catalyst is prepared in situ by the reaction of the tertiary amine with benzyl chloride.

* * * * *